(12) United States Patent
Rathjen (10) Patent No.: US 8,591,031 B2
(45) Date of Patent: Nov. 26, 2013

(54) DEVICE AND METHOD FOR DETERMINING THE VISUAL FIELD

(75) Inventor: Christian Rathjen, Bremen (DE)

(73) Assignee: Ziemer Ophthalmic Systems AG (CH)

( * ) Notice: Subject to any disclaimer, the term of this patent is extended or adjusted under 35 U.S.C. 154(b) by 76 days.

(21) Appl. No.: 13/297,672

(22) Filed: Nov. 16, 2011

(65) Prior Publication Data

US 2012/0133890 A1 May 31, 2012

Related U.S. Application Data

(60) Provisional application No. 61/415,428, filed on Nov. 19, 2010.

(51) Int. Cl.
*A61B 3/14* (2006.01)
*A61B 3/00* (2006.01)

(52) U.S. Cl.
USPC .......................................... 351/209; 351/246

(58) Field of Classification Search
USPC ................................................ 351/200–246
See application file for complete search history.

(56) References Cited

U.S. PATENT DOCUMENTS

| 7,309,128 B2 | 12/2007 | Cappo et al. | |
| 2002/0191153 A1* | 12/2002 | Wei et al. | 351/243 |
| 2009/0153796 A1* | 6/2009 | Rabner | 351/201 |
| 2010/0238404 A1* | 9/2010 | Newman et al. | 351/208 |

FOREIGN PATENT DOCUMENTS

| DE | 1963161 | 6/1967 |
| DE | 19538382 | 4/1996 |
| EP | 0045897 | 2/1982 |

* cited by examiner

*Primary Examiner* — Mohammed Hasan
(74) *Attorney, Agent, or Firm* — Ostrolenk Faber LLP (57) ABSTRACT

A device (1) for determining the visual field comprises a screen (11) for displaying test patterns, an eye monitoring module (13) for capturing eye movements of a patient (20), and a processing module (10) for determining the visual field of the patient on the basis of the eye movements when the test patterns are displayed. The device (1) moreover comprises a mirror (12), which is aligned parallel to the bipupillary line of the patient (20) for determining the visual field, for deflecting the test patterns from the screen (11) to the eyes. The use of the mirror (12) aligned parallel to the bipupillary line of the patient results in a particularly compact design of the device (1) for determining the visual field, which device makes the same geometric and optical measurement conditions possible for both eyes.

16 Claims, 5 Drawing Sheets

DEVICE AND METHOD FOR DETERMINING THE VISUAL FIELD

CROSS-REFERENCE TO RELATED APPLICATIONS

This application claims benefit of and priority to U.S. Provisional Application Ser. No. 61/415,428, filed Nov. 19, 2010, the entire contents of which are hereby incorporated by reference herein.

BACKGROUND

The present invention relates to a device and a method for determining the visual field of a patient. The present invention more particularly relates to a device and a method for determining the visual field of a patient based on viewing directions of the patient that are determined when test patterns are displayed on a screen.

RELATED ART

Devices for determining the visual field of a patient are referred to as perimeters. Perimeters are used particularly in the case of glaucoma for capturing losses in the visual field. In the case of static perimetry, the patient generally fixes a central fixation target and presses a button as soon as he sees a punctiform light stimulus in the periphery. In the case of kinetic perimetry, the light stimulus is moved. The location and the light intensity of the stimulus are provided as measurement data. The visual field is established in the form of a visual field chart on the basis of a plurality of such point projections.

U.S. Pat. No. 7,309,128 describes a method and a device for measuring the visual field, in which the patient is presented with fixation and test images that are controlled by a computer. The fixation images are displayed, separately for each eye, to the patient on two displays. As per U.S. Pat. No. 7,309,128, separate mirrors are used to separately deflect the fixation images onto the two eyes. The test image for determining the visual field is shown to the patient on a screen that is arranged perpendicularly to the visual axes of the patient. In order to determine as precisely as possible the region between points that correspond to seen and not-seen test images, the computer automatically tests additional points in this region. U.S. Pat. No. 7,309,128 moreover uses a so-called eyetracker with an image sensor, e.g. a light-sensitive sensor or sensor array or a charge coupled device (CCD) camera for capturing images of the eyes.

DE 2 427 733 describes an instrument for determining the visual field, having three sidewalls that provide the instrument with an approximately triangular outline. One of the sidewalls contains a screen on which a fixed and a manually displaceable test mark can be displayed. A further sidewall contains a binocular through which the patient can see the screen via a mirror attached to the third sidewall. As a result of the triangular arrangement of the sidewalls, the eyes of the patient have a different distance from the mirror, but DE 2 427 733 lists as advantages that the examining person is able to see the patient side-on and assess whether the patient is sufficiently attentive, and that the distance between the patient and the test markers is significantly increased by the mirror without this requiring an excessively large instrument. However, manual positioning of test marks and subjective capturing of the visual field generally do not supply very precise results.

SUMMARY

It is an object of the present invention to propose a device and a method for determining the visual field of a patient that overcome at least specific disadvantages of the prior art. More particularly, it is an object of the present invention to propose a device and a method for determining the visual field of a patient that allow a compact design of the device and mobile use.

As per the present invention, these goals are achieved by the elements of the independent claims. Further advantageous embodiments moreover emerge from the dependent claims and from the description.

A device for determining the visual field includes a screen for displaying test patterns, an eye monitoring module for capturing eye movements of the patient when the latter observes the screen, and a processing module configured to determine viewing directions of the patient on the basis of the eye movements when the test patterns are displayed and establish the visual field of the patient on the basis of the viewing directions determined for the test patterns.

The present invention more particularly achieves the aforementioned goals by virtue of the fact that the device for determining the visual field moreover includes a mirror, which is aligned parallel to the bipupillary line of the patient for determining the visual field, for deflecting the test patterns from the screen to the eyes. Here the bipupillary line is a straight line through the center of the two pupils, with an erect posture of the patient and hence a horizontal alignment of the bipupillary line being presupposed and assumed for determining the visual field. Using the mirror aligned parallel to the bipupillary line of the patient, results in a particularly compact design of the device for determining the visual field, which makes the same geometric and optical measurement conditions possible for both eyes.

The screen for determining the visual field is preferably positioned lying on a horizontal support surface, with a screen display area, aligned substantially horizontally, that is facing away from the support surface. The screen is preferably a flat screen. The horizontal alignment of the screen display area when the screen is positioned in a lying fashion makes a low center of gravity and stable positioning of the device possible.

In one embodiment, the screen and the mirror are coupled, rotatable about an axis, along one of their longitudinal sides such that a mirroring surface of the mirror and a screen display area of the screen can, whilst facing one another, be folded open or shut. The flexible folding shut allows simple transportation, which is advantageous for applications in mobile use, for example, in retirement homes and hospitals. The rotatable mirror in this case allows particularly simple assembly and disassembly of the device for determining the visual field.

In one embodiment, the device includes stray-light protection with two stray-light protective screens that are respectively aligned substantially perpendicular to the rotational axis mentioned above. The two stray-light protective screens are respectively connected to the screen and the mirror in an edge region of the screen and the mirror, and arranged in an aperture angle between the screen and the mirror. In a variant that can be folded open and shut, the stray-light protection is configured to open in the aperture angle that results from the screen and the mirror being folded open. In a variant that cannot be folded open and shut, the stray-light protection is part of a static housing of the device.

In a further embodiment, the device includes a sight screen that can be positioned between the screen display area and the patient for determining the visual field such that the screen display area is not directly visible to the patient. The sight screen prevents falsification of the visual field test by light stimuli that are displayed on the screen and perceived directly there by the patient.

In one embodiment, the device includes a distance sensor for determining the relative distance between the eyes and the mirror, and the processing module is configured to establish the visual field of the patient depending on the relative distance of the eyes. By dynamically determining and taking account of the distance between the eyes and the screen, different positions of the mirror are possible when the device is unfolded, without this noticeably influencing the accuracy of the visual field test.

In a further embodiment, the processing module is configured to display a sequence of test patterns on the screen, respectively determine the viewing direction of an eye of the patient when the test patterns are displayed and store said viewing direction assigned to the respective test pattern, and establish the visual field of the patient for one or both eyes on the basis of the viewing directions captured for the sequence of test patterns. As a result of automatically generating a sequential sequence of test patterns and establishing the visual field of the patient in a manner based thereon, a particularly efficient visual field test is made possible, which more particularly is also suitable for being carried out independently by the patient. By way of example, the processing module is designed to dynamically adapt the sequence of test patterns depending on viewing directions captured for the patient.

In one embodiment, the processing module is configured to display one or more reference patterns on the screen. The eye monitoring module is configured to capture reference patterns reflected from an eye of the patient and the processing module is configured to determine the viewing direction of an eye of the patient, respectively based on the reflected reference pattern.

In one embodiment, the processing module is configured to capture a reaction time of the patient, respectively depending on the eye movements, when the test patterns are displayed and to store spatially dependent reaction times in the visual field of the patient.

In a further embodiment, the eye monitoring module is arranged on a side of the mirror facing away from the patient during the visual field test, and the mirror has a point, placed in front of the eye monitoring module and permeable to light at least specific wavelengths, for determining the eye movements. In a particularly simple embodiment, the point permeable to light is embodied as a bore in the mirror.

In another embodiment, the eye monitoring module is arranged on a side of the mirror facing toward the patient during the visual field test and the eye monitoring module is designed to determine the eye movements via the mirror.

In another embodiment, the eye monitoring module, for determining the visual field, is arranged with a direct line of sight to the eyes of the patient and outside of the mirroring surface of the mirror.

In various embodiments, the eye monitoring module includes one or two image sensors and is accordingly designed to establish the eye movements of an eye in a monoscopic or stereoscopic fashion.

In a further embodiment, the mirror is embodied with a non-planar, e.g. concave and/or segmented, mirror surface for increasing the field angle.

In addition to the device for determining the visual field, the present invention moreover relates to a method for determining the visual field, in which test patterns are displayed on a screen, eye movements of a patient are captured, viewing directions of the patient are determined on the basis of the eye movements when the test patterns are displayed, and the visual field of the patient is established on the basis of the viewing directions determined for the test patterns, wherein the test patterns are deflected from the screen to the eyes via a mirror aligned parallel to the bipupillary line of the patient for determining the visual field.

BRIEF DESCRIPTION OF THE DRAWINGS

In the following text, an embodiment of the present invention is described on the basis of an example. The exemplary embodiment is illustrated by the following attached figures, in which.

DETAILED DESCRIPTION OF THE EMBODIMENTS

In FIGS. 1, 1a, 2, 3a, 3b and 3c, reference sign 1 relates to an ophthalmological device for determining the visual field of a patient 20.

As illustrated schematically in FIGS. 1, 1a, 2, 3a, 3b and 3c, the ophthalmological device 1 includes a screen 11 with a screen display area 110, a mirror 12 with a mirroring surface 120, a processing module 10 and an eye monitoring module 13 (eyetracker).

In one variant, the device 1 comprises an optional distance sensor 18 for determining the relative distance between the eyes 2, or the eye 2 to be tested, of the patient 20 and the mirror 12. In the case of stereoscopic embodiments of the eye monitoring module 13 in particular, the distance sensor 18 is not embodied as hardware as a sensor element but as part of the processing module 10, i.e. distance values are established by a distance function in the processing module 10 on the basis of the images captured by the eye monitoring module 13. A distance sensor 18 is rendered unnecessary if the position of the eyes 2 is sufficiently precisely fixed by a head rest and/or an (optional) chin rest 15, 16 and the distance is calibrated.

The processing module 10 is connected to the screen 11, the eye monitoring module 13 and the optional distance sensor 18, and comprises one or more operational processors with data and program memory. The processing module 10 includes programmed software modules with program code for controlling the processors such that these execute functions that are described in more detail below. The program code is stored on an accessible, computer-readable medium that is connected to the processors in a fixed or removable fashion. A person skilled in the art will understand that the functions of the processing module 10 can be partly or wholly executed by hardware components in alternative embodiment variants.

The processing module 10 is substantially designed to generate test patterns for determining the visual field and display them on the screen 11, to accept, store and evaluate eye movements of the patient 20 captured by the eye monitoring module 13, and to accept, store and evaluate the relative distance between the eyes 2 of the patient 20 and the mirror 12 from the optional distance sensor 18.

Figure 1:
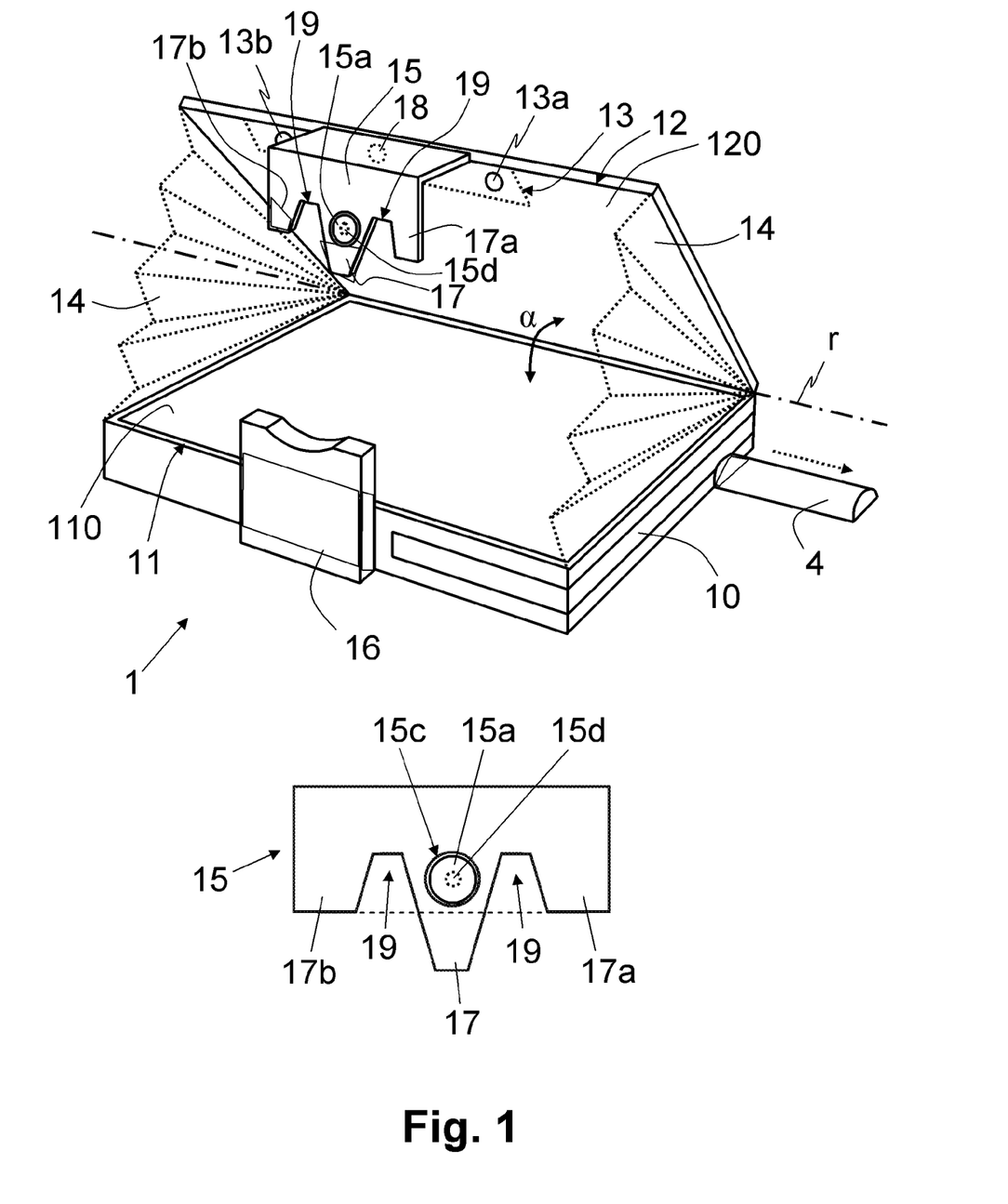
FIG. 1 shows a perspective and schematic illustration of a device for determining the visual field, including a screen for displaying test patterns and a mirror for deflecting the test patterns from the screen to the eyes of a patient.
Figure 1A:
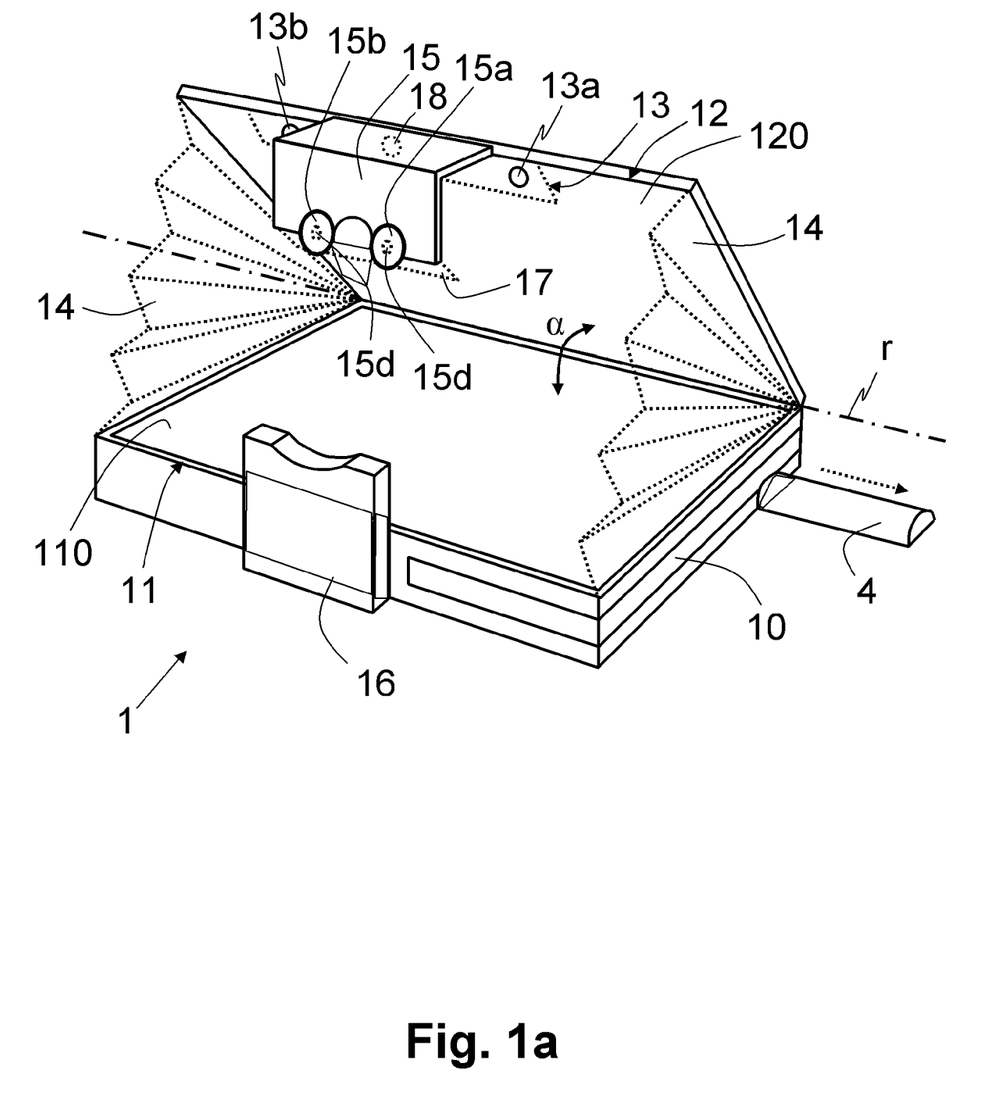
FIG. 1a shows a perspective and schematic illustration of an embodiment of the device with two lenses for a binocular visual field test.

In one embodiment, the ophthalmological device 1 includes one or more adjustable lenses 15a, 15b, as illustrated schematically in FIGS. 1, 1a; the focal lengths of said lenses can be adjusted manually or automatically by the processing module 10.

The screen 11 is embodied as an active, self-illuminating flat screen or as a passive, externally illuminated flat screen. In one embodiment, the screen 11 is embodied to be touch sensitive, as a so-called touch or multitouch screen, and serves as an input element for entering patient data, measurement parameters and control commands, etc. In an alternative embodiment, or in addition thereto, the device 1 includes a wireless and/or contact-based data interface for data interchange with an external personal computer (PC), which is used for controlling the device 1 and/or capturing and storing test results. The ophthalmological device 1 or the external PC preferably has an external screen in addition to the device 1 for displaying measurement results and/or entered control commands and control parameters.

As illustrated in FIGS. 1, 1a, 2, 3a, 3b and 3c, the screen 11 and the mirror 12 are interconnected on one of their longitudinal sides along the axis r. The screen 11 and the mirror 12 are preferably, but not necessarily, rotatably interconnected via a swivel joint, for example a hinge, about the rotational axis r. The rotatable coupling between the screen 11 and the mirror 12 allows the ophthalmological device 1 to be folded shut and open, like in the case of a laptop computer. However, in the present ophthalmological device 1 the screen 11 is designed to be positioned in a substantially horizontal, flat-lying fashion and forms the basis of the device 1.

Figure 3A:
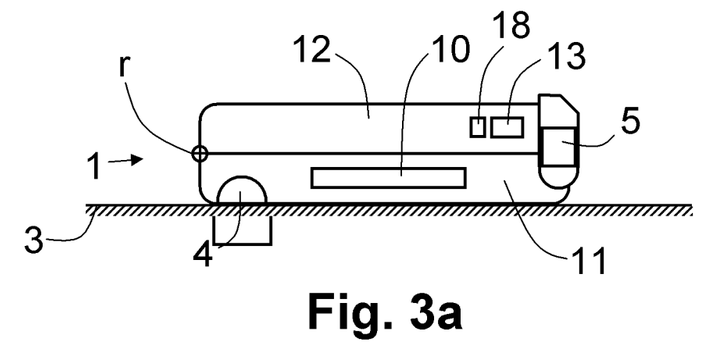
FIG. 3a schematically shows a cross-sectional view of a foldable embodiment of the device for determining the visual field, in the closed, folded-shut state.

In the closed, folded-shut state, the screen 11 and the mirror 12 are aligned substantially parallel to one another, with the screen display area 110 and the mirroring surface 120 of the mirror 12 being opposite and facing one another; this can be seen in FIG. 3a.

In the operating mode for determining the visual field, the mirror 12 is folded open and an angle α is formed between the screen display area 110 and the mirroring surface 120 of the mirror 12. For determining the visual field, the angle α for example lies in the range between 30° and 60°, with preferred angular positions being indicated to the user by a latching mechanism.

Figure 3B:
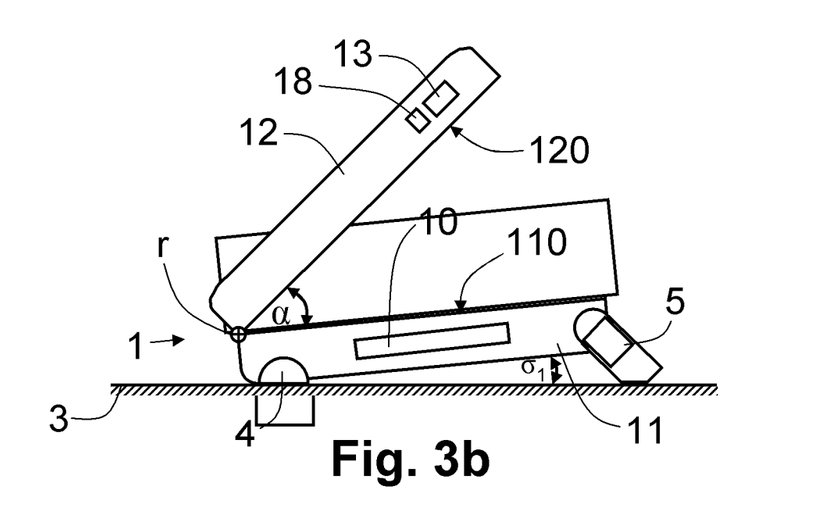
FIGS. 3b and 3c schematically show cross-sectional views of the foldable embodiment of the device in the folded-open state, with the screen being positioned obliquely at different angles to the horizontal support surface.
Figure 3C:
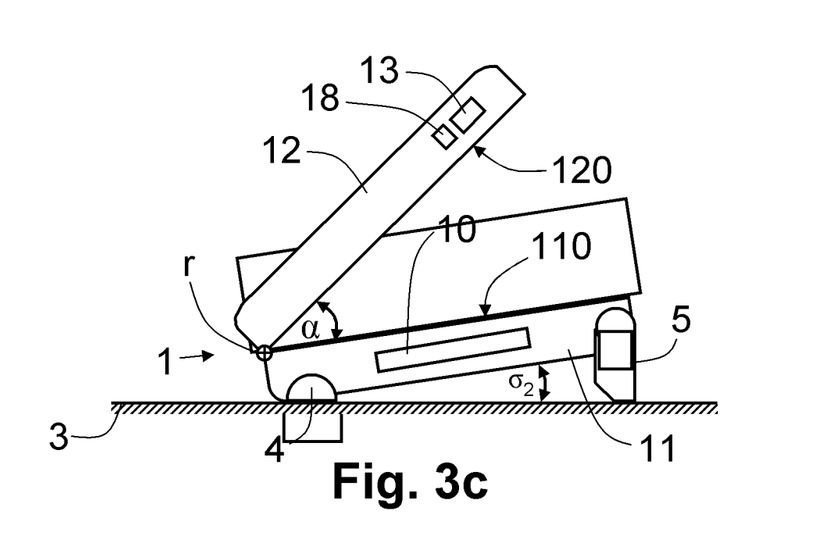

As illustrated schematically in FIGS. 3a to 3c, the ophthalmological device 1 in one embodiment includes a rotatable carrying handle 5, which is attached to the longitudinal side of the screen 11 opposite to the rotational axis r and which runs substantially parallel to the rotational axis r. The carrying handle 5 is rotatable about an axis running parallel to the rotational axis r and designed such that the screen 11, and hence the screen display area 110, can be positioned obliquely with respect to the horizontal support surface 3 at a selectable angle $\sigma_1$, $\sigma_2$ by corresponding positioning of the carrying handle 5, with this angled position within the meaning of the present invention still being considered as a substantially horizontal alignment of the screen 11 or the screen display area 110 since the angle $\sigma_1$, $\sigma_2$ for example does not exceed 15°.

The basis of the device 1 formed by the screen 11 is stabilized by the optional support legs 4, which are embodied rotatable about a horizontal axis parallel to the rotational axis r and can be secured by latching. By way of example, the support legs 4 have a semi-circular cross section. In one variant, the support legs 4 can moreover be pulled laterally out of the base body of the screen 11, along an axis parallel to the rotational axis r, as illustrated schematically in FIGS. 1, 1a. The support legs 4 moreover or alternatively serve as handles that the patient can hold or rest his hands upon.

In one variant, the ophthalmological device 1 moreover includes two lateral stray-light protective screens 14 as stray-light protection, as illustrated schematically in FIGS. 1, 1a. The stray-light protective screens 14 are aligned substantially perpendicular to the rotational axis r and are respectively attached to the screen 11 and the mirror 12 in lateral edge regions. In the version of the device 1 that can be folded shut and open, the stray-light protective screens 14 have a flexible design, for example they are folded or provided with a plurality of moveable disk elements, arranged in parallel, like in an iris stop, and are designed to open, optionally by unfolding or sliding apart, on both sides when the mirror 12 is folded open in the aperture angle α between the screen 11 and the mirror 12.

FIGS. 1, 1a show that the ophthalmological device 1 moreover includes one, e.g. adjustable, sight screen 17, which, for the purpose of determining the visual field, is or can be positioned between the screen display area 110 and the eyes 2 of the patient, for example by correspondingly being swiveled-in or rotated, such that the patient 20 cannot see the screen display area 110 directly, but only via the mirror 12. In addition to a sight screen 17 or as an alternative thereto, the processing module 10 is used to check whether there is a reaction to the correct light stimulus on the basis of the eye movements captured by the eye monitoring module 13.

Figure 2:
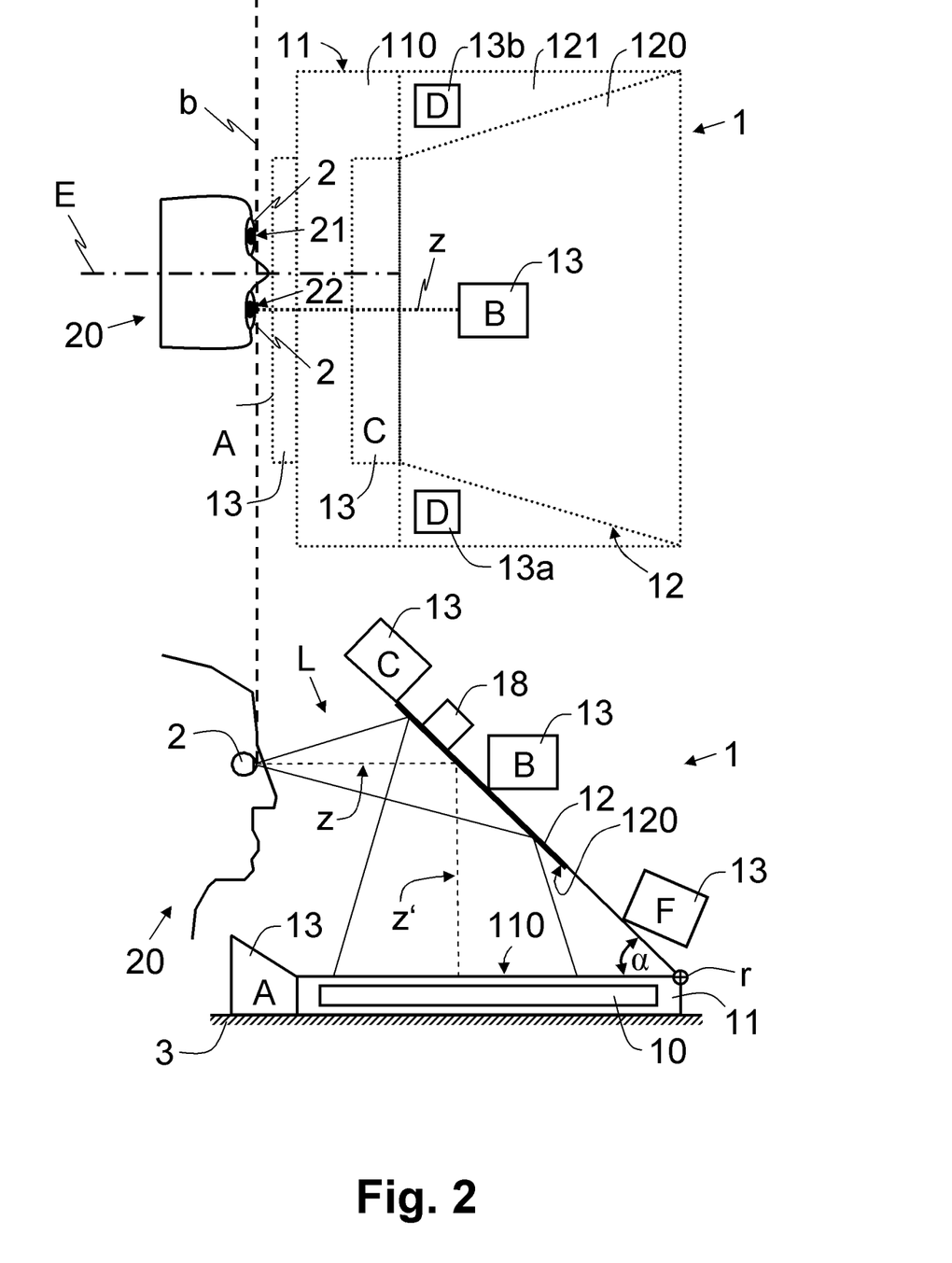
FIG. 2 shows a cross section (lower part) and plan view (upper part), which schematically illustrate the alignment of the mirror parallel to the bipupillary line of the patient and the deflection of the test patterns from the screen to the eyes of the patient via the mirror.

In the lower part, FIG. 2 schematically illustrates, in a cross section, the deflection of the light beams L of the test pattern, displayed on the screen 11, to the eyes 2 of the patient 20 via the folded-open mirror 12. FIG. 2 moreover illustrates the substantially parallel alignment of the mirror 12 to the bipupillary line b of the patient 20, which is a straight line that interconnects the centers of the pupils 21, 22 of the patient 20, as can be identified from the schematic plan view of the head of the patient 20 in the upper part of FIG. 2. In the case of a planar embodiment of the mirror surface 120, the mirror surface 120 is accordingly also substantially aligned parallel to the bipupillary line b of the patient 20. The screen 11 or the screen display area 110 is preferably arranged and aligned such that a beam z', projected along the visual axis z and deflected by the mirror 12, impinges substantially perpendicularly on the screen surface 110, and hence both the screen 11, or the screen display area 110, and the mirror 12, or the mirror surface 120, are arranged parallel to the bipupillary line b.

In an alternative embodiment, the mirror surface 120 is embodied in a concave fashion and/or with a segmented mirror surface 120 for increasing the field angle and, connected to this, an extended visual field test. Even in the case of such a concave or segmented design of the mirror surface 120, the alignment of the mirror 12 within the meaning of the present invention should still be considered to be aligned substantially parallel to the bipupillary line b of the patient 20 since an optical axis aligned normally to the mirror surface 120 runs in the symmetry plane E during the visual field test, which symmetry plane is arranged between the eyes 2 of the patient 20 and aligned perpendicularly to the bipupillary line b of the patient 20.

In one variant, the processing module 10 is designed to adjust the focal length of the adjustable lenses 15a, 15b automatically in the case of test patterns with light reflex marks in the outer region of the visual field so that the patient 20 can also see these imaged in focus. This is advantageous, in particular, in the embodiment variant with a mirror surface 120 with a concave and/or segmented embodiment, where the visual field range is increased by the extended field angle. In an alternative embodiment, a Fresnel lens or a diffractively optical element is applied, for this purpose, on or above the screen display area 110.

FIG. 2 moreover illustrates different arrangements of the eye monitoring module 13. The eye monitoring module 13 includes one image sensor (camera) in the case of a monoscopic embodiment and two image sensors (cameras) 13a, 13b in the case of a stereoscopic embodiment.

Reference sign A relates to an arrangement of the eye monitoring module 13, in which one or two image sensors (cameras), arranged on the front side of the screen 11 facing away from the rotational axis r, follow and capture the eye movements of the patient 20 via the mirror 12.

Reference signs B and F relate to arrangements in which one or two image sensors (cameras) of the eye monitoring module 13 are arranged on the rear side of the mirror 12 facing away from the mirror surface 120, and follow and capture the eye movements of the patient 20 through a light-permeable point in the mirror 12. By way of example, the light-permeable point is embodied as a bore or as a coating on the mirror surface 120 that is permeable to certain wavelengths of light. In the arrangement denoted by reference sign B, the image sensor(s) (camera(s)) of the eye monitoring module 13 is/are for example arranged at the point where the visual axis z penetrates the mirror 12 when the angle α is set accordingly. In the arrangement denoted by reference sign F, the image sensor(s) (camera(s)) of the eye monitoring module 13 is/are arranged below the visual axis z and capture(s) the eye movements of the patient obliquely from below. The arrangement denoted by F is advantageous in that capturing the eye movement from obliquely below generally provides better, i.e. more precise and clearer, results than captures from above the visual axis z. Moreover, certain eye monitoring modules 13, particularly in the case of stereoscopic designs, require working distances from the eyes 2 that do not allow a practical integration into the device 1, particularly into a support of the mirror 12, whereas the arrangement denoted by F allows greater working distances and hence an integration into the device 1 or into the support of the mirror 12. Moreover, the arrangement denoted by F enables a simpler design of the mirror 12 because the eye monitoring module 13 can be arranged in a region of the mirror 12 that need not necessarily have a mirroring surface 120 for the functionality of the device 1, and so the mirror 12 can in fact have a transparent design in the region of the eye monitoring module 13 and need not be provided with a bore.

Reference signs C and D relate to arrangements in which one or two image sensors (cameras) 13a, 13b of the eye monitoring module 13 are arranged outside of the mirroring surface 120 of the mirror 12, and follow and capture the eye movements of the patient 20 in a direct line of sight during the visual field test. In the arrangement denoted by C, the eye monitoring module 13 is arranged on the front side line of the mirror 12 facing away from the rotational axis r. In the arrangement denoted by D, preferably two image sensors (cameras) 13a, 13b are each arranged in a lateral, preferably non-mirroring edge region 121 of the mirror 12, on the side of the mirror 12 facing the patient 20 during the visual field test.

In one variant, the processing module 10 comprises a calibration function that allows or carries out a geometric and/or radiometric calibration of the device 1 or the method for determining the visual field. By way of example, the calibration function is carried out on the basis of measurement data captured by an image sensor 15d, e.g. a light-sensitive sensor or sensor array or a camera. By way of example, the image sensor 15d is fixedly or removably attached to the point at which the eye of the patient is positioned, e.g. on the head rest 15, in or on the bores 15c for the lenses 15a, 15b, for example such that it can be swiveled away. The measurement data captured by the image sensor 15d substantially comprise the calibration or test image patterns, emitted by the screen 11 and deflected by the mirror 12, from which the calibration function generates base values for calibrating the device 1 or the method for determining the visual field. By way of example, the base values comprise local brightness values and brightness distributions of the emitted and captured patterns and, as a result thereof, current emission properties of the screen 11 or the screen display area 110, positioning of the patterns and, as a result thereof, the relative alignment to the patterns, and/or the size of and hence the distance to the patterns. The determined base values are taken into account during the visual field test, for example by being included in calculating or determining thresholds and/or by adjusting the emission of the test patterns, for determining the visual field, in respect of local brightness, size and/or position of the display on the screen display area 110. In an alternative or additional variant, the local distribution of the emission brightness, i.e. the radiometric base values of the screen 11, is captured by means of radiometric sensors placed onto the image display area 110.

Figure 4:
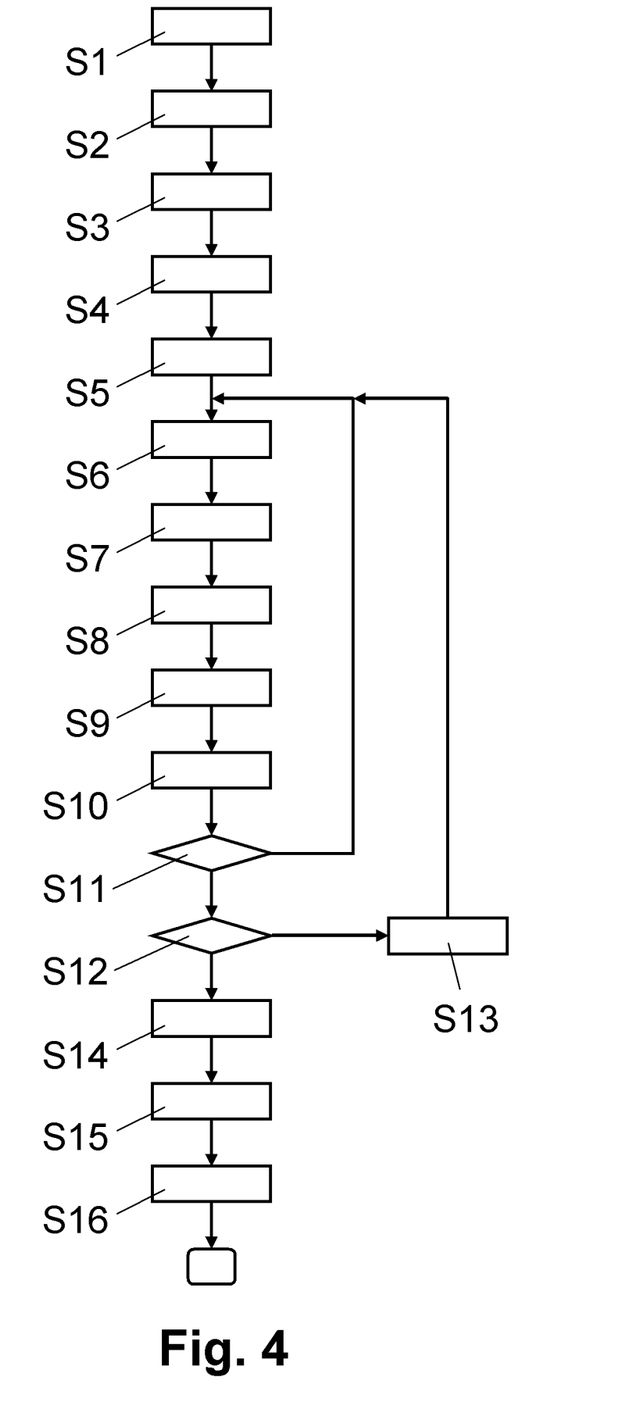
FIG. 4 shows a flowchart that illustrates an example of a sequence of steps for a method for determining the visual field of a patient.

In the following paragraphs, an example of a sequence of steps for carrying out the ophthalmological method for determining the visual field of a patient 20 by means of the device 1, and the functions of the processing module 10, is described with reference to FIG. 4.

The visual field is typically determined separately for each eye 2 of the patient, with the processing module 10, e.g. automatically, closing a screen (not illustrated) for the unaffected eye 2, which screen is for example integrated into the lens(es) 15a, 15b or arranged up- or downstream thereof.

In step S1 of the ophthalmological method, the ophthalmological device 1 is switched on and, in the foldable version, positioned on a horizontal support surface 3, folded open and, optionally, the support legs 4 are pulled out.

In step S2, the visual field test to be carried out is selected by input means, for example via the touch-sensitive screen 11, a keyboard or operating buttons, for example by selecting one of a number of defined sequences of test patterns, and patient data is entered, for example identification data and specifications in respect of vision or refractive corrective requirements.

In step S3, the patient 20 is positioned with respect to the device 1; here the chin is positioned on the chin rest 16 and the position of the lenses 15a, 15b is matched to the height of the eyes, either by adjusting the height of the chin rest 16 or by setting the angle α between mirror 12 and screen 11, for example by appropriate positioning of the head rest 15, which is embodied as a visor. Alternatively, or in addition thereto, the head of the patient is preferably supported on or against the head rest 15, and thus there is relative positioning, and a fixed distance, between the eyes 2 and the device 1 or the eyes 2 and the mirror 12 and the screen display area 110. FIG. 1 and, additionally, a detailed view show that in one embodiment variant the visor or head rest 15, with a symmetric design, has two recesses 19 for positioning the nose of the patient, which recesses are respectively arranged on both sides of a bore 15c, next to the bore 15c which is provided with the lenses 15a; this arrangement is dependent on whether the left or right eye 2 should be examined. Here the respective eye 2 not being examined is covered by one of the tabs 17a, 17b of the visor, while the eye 2 to be examined is positioned in front of the bore 15c with the lenses 15a and looks onto the mirror 12. In this embodiment, the sight screen 17 is arranged below the bore for the lenses 15a, 15b between the two recesses 19. By way of example, the sight screen 17 corresponds to the recesses 19 in terms of area and shape, as indicated in the detailed view by the dashed line. Moreover, in the illustrated embodiment, the sight screen 17 respectively has one common lateral edge with the recesses 19; in the region of the recesses 19, these lateral edges respectively form an inner edge and in the region of the sight screen 17 these form an outer edge. The two tabs 17a, 17b of the visor also serve as a sight screen such that the screen display area 110 cannot be seen directly by the patient 20 but is only visible via the mirror 12.

In an alternative embodiment, for example as an interchangeable visor, two bores with lenses 15a, 15b are provided as illustrated in FIG. 1a, which lenses are, like in spectacles, respectively arranged to the left and right of a single recess 19 for the nose, and so it is optionally possible to examine both eyes 2 at the same time (in a binocular fashion) or else to only examine one of the two eyes 2, without having to displace the position of the head or nose for this. The bipupillary line b of the patient 20 is aligned substantially parallel to the rotational axis r and hence to the mirror 12 and the screen 11.

In step S4, possibly required dioptre-corrections for the patient 20 are undertaken by adjusting the lenses 15a, 15b either manually or automatically by the processing module 10. Here, a fixation pattern and/or reading-test images are displayed on the screen 11 for the patient 20 and deflected to his eyes 2 via the mirror 12. Further fine tuning of the alignment of mirror 12 and screen 11 are undertaken. If required, the angle of inclination $\sigma_1$, $\sigma_2$ of the screen 11 is adjusted by suitably positioning the carrying handle 5.

After successfully positioning, aligning and optically setting the ophthalmological device 1 with respect to the patient 20 and his eyes 2, the selected sequence for determining the visual field is started in step S5, for example by pressing a button or touching the screen 11. Here, the current relative distance between the eyes 2 of the patient 20 and the mirror 12 or the screen display area 110 is established and stored by means of the distance sensor 18. Alternatively, the distance is determined on the basis of the current angle $\alpha$ between screen 11 and mirror 12 and the defined geometry of the device 1.

In step S6, the first test pattern of the sequence for determining the visual field is generated on the screen 11 by the processing module 10. The displayed test pattern is guided to the eyes 2 of the patient 20 from the screen display area 110 via mirroring reflection on the mirror surface 120 of the mirror 12. The processing module 10 adjusts the focal length of the lenses 15a, 15b where necessary when the test pattern generates light stimuli in the outer field angle range, particularly in an embodiment with an extended field angle.

The test patterns each include one light stimulus, with differing size and brightness, arranged at a defined point for determining the visual field. In addition to the actual light stimulus, the test patterns preferably also include static fixation patterns, for example in the form of fixation or target marks, and reference patterns, for example Placido patterns, that are reflected on the eye 2 to be observed and captured by the eye monitoring modules 13 for determining eye movements and viewing directions. The processing module 10 is moreover configured to generate and display alternative fixation patterns if the fixation or target mark, typically arranged centrally, cannot be seen by the relevant eye 2 of the patient 20 as a result of a visual defect. In a further variant, the ophthalmological device 1 includes external fixation targets that are arranged outside of the region where the visual axis z penetrates the mirror 12 if the angle $\alpha$ is set appropriately and that are mirrored onto the visual axis z via a partly transparent mirror. For other examinations, e.g. neurophysiological examinations, the head rest 15 can expediently be removed, and the eye monitoring module 13 and the processing module 10 are designed to capture and track both eyes 2 (simultaneously).

In a further variant, the ophthalmological device 1 includes a keratometer for measuring, establishing and storing the corneal topology of the patient, preferably with the aid of the aforementioned Placido patterns and image sensors (cameras) 13a, 13b of the eye monitoring module 13.

In step S7, the processing module 10 obtains the eye movements captured by the eye monitoring module 13 when the test pattern is displayed. In the process, the processing module 10 for example stores a sequence of images of the eye 2 to be measured.

In step S8, the processing module 10 establishes the viewing direction of the patient 20 when the test pattern is displayed as a result of the captured eye movements. Moreover, the processing module 10 uses the image data captured by the eye monitoring module 13 to establish the relative distance of the eyes 2 from the device or from the mirror 12 if the distance has not been defined a priori, for example by head and/or chin rests 15, 16. Here the processing module 10 for example evaluates the stored image sequence with the captured eye moments on the basis of the distance between the eyes 2 of the patient 20 and the mirror 12. The image sequence allows precise temporal and spatial association between the test pattern being displayed and the eye movements of the patient 20.

If an eye movement of the patient 20 that is correlated with the test pattern in time and space can be detected in the direction of the light stimulus of the relevant test pattern, the position of the light stimulus perceived by the patient 20 in the test pattern is captured and stored in step S9 as a positive point in a geometric visual field chart for the patient 20. In one variant, the relevant position is otherwise likewise captured as a negative point. Hence the processing module 10 is used to establish and check, on the basis of the eye movements captured by the eye monitoring module 13, whether there is a reaction to the light stimulus and whether there is a reaction to the correct light stimulus.

In step S10, the processing module 10, in the case of a positive reaction to the test pattern, establishes the reaction time of the patient 20 by establishing the period of time between displaying the test pattern and the detected correlated eye movement of the patient 20 in the direction of the light stimulus in the relevant test pattern. Here, the processing module 10 for example evaluates the stored image sequence with the captured eye movements. The reaction time is stored in the visual field chart, associated with the captured position of the light stimulus.

In step S11, the processing module 10 checks whether the test pattern sequence started in step S5 has been worked through or whether the sequence includes further test patterns to be displayed, with light stimuli in other positions. If further test patterns should be displayed, the processing module 10 continues with the method in step S6, otherwise with that in step S12.

In step S12, the processing module 10 checks whether boundary regions in the generated visual field chart, with adjoining zones with positively or negatively marked points, require resolving at a higher measurement resolution, for example compared to a defined accuracy threshold, and/or whether the visual field chart has regions with apparently contradictory positive and negative points. If a refined and/or checked visual field test is required, the processing module 10 proceeds with the method in step S13; otherwise it proceeds with that in step S14. It should be noted here that the brightness of the light stimulus is varied and different individual or numerous punctiform positive/negative values or positive/negative charts are generated for different brightness levels, in which charts the light stimuli perceived or not perceived in the test pattern are displayed or stored as positive or negative points for each brightness level. The processing module 10 generates a visual field chart, embodied as a sensitivity map, on the basis of the positive/negative charts of different brightness levels, with the sensitivity for example being specified in dB, or said module generates punctiform sensitivity values or partial visual field charts for one or more points.

In step S13, the processing module 10 generates additional sequences with test patterns for the questionable regions of the visual field chart determined in step S11—these additional sequences have a refined grid of light stimuli in the regions to be examined in more detail—and then continues with the method in step S6.

In step S14, the processing module 10 stores the measurement results, i.e. the generated visual field chart or the punctiform sensitivity values or the partial visual field charts assigned to the patient 20, with date and time. By way of example, the measurement results include a table with the positive, and optionally the negative, positions, which are determined by Cartesian and/or polar coordinates, and with reaction times that are associated with the positive points. In one variant, the measurement results, more particularly the partial or complete visual field charts, are generated as a displayable image, in which the positive and optionally negative positions, contrast, luminescence, latency times, reaction times and/or sensitivity values are visually displayed in a two-dimensional chart in respect of brightness and/or color, i.e. wavelength-dependent, for example using different colors, and value specifications, which are reproduced numerically or with different brightness or color intensity.

In step S15, the processing module 10 outputs the measurement results, for example the generated visual field chart(s), as a display on the screen 11 and/or as a printout on a printer connected to the device 1.

In optional step S16, the processing module 10 transfers the measurement results, for example the generated visual field chart(s), as a digital file via a communication link to a communication terminal, for example, to a responsible ophthalmologist and/or a patient database, for example by means of a communication module via a device interface, e.g. contactlessly via Bluetooth or in a contact-based manner via USB, a communication network, e.g. wirelessly via a WLAN or a mobile cellular network or in a wired manner via a LAN, WAN, ISDN, POTS or another communication network, including the Internet.

In further embodiments the processing module 10 is configured to control the ophthalmological device 1 for carrying out reading and/or sight tests, in which the ability to see and read, and the recognition and reading speed, are established.

Finally, it should also be noted at this juncture that the processing module 10 is designed in a variant for carrying out different stored measurement programs, which can be selected and configured by the user and have different test strategies, with different threshold strategies for establishing the sensitivities and/or with different measurement point grids. By way of example, such strategies may serve (use-dependent) for reducing the measurement time or for improving the delineation of regions with visual field defects.

Finally, it should be stated here that although computer program code was assigned to specific functional modules in the description and although the steps were presented as being executed in a specific sequence, a person skilled in the art will understand that the computer program code can be structured differently and the sequence of at least specific steps can be modified without departing from the scope of the protection.

Although the present invention has been described in relation to particular embodiments thereof, many other variations and modifications and other uses will become apparent to those skilled in the art.

What is claimed is:

1. A device for determining a visual field of a patient, comprising:
 a screen for displaying test patterns,
 a mirror, which is aligned parallel to the bipupillary line of the patient for determining the visual field, for deflecting the test patterns from the screen to the eyes of the patient,
 an eye monitoring module for capturing eye movements of the patient, and
 a processing module configured to determine viewing directions of the patient on the basis of the eye movements when the test patterns are displayed and establish the visual field of the patient on the basis of the viewing directions determined for the test patterns.

2. The device as claimed in claim 1, wherein the screen is positioned lying on a horizontal support surface, and includes a screen display area, aligned substantially horizontally, that is facing away from the support surface.

3. The device as claimed in claim 1, wherein the screen and the mirror are rotatably coupled, rotatable about an axis along one of their longitudinal sides such that a mirroring surface of the mirror and a screen display area of the screen face one another, and the screen and mirror are movable between an open position and a closed position.

4. The device as claimed in claim 3, further comprising two stray-light protective screens that are respectively aligned substantially perpendicular to the axis and connected to the screen and the mirror in an edge region of the screen and the mirror, and arranged in an aperture angle between the screen and the mirror.

5. The device as claimed in claim 2, further comprising a sight screen positioned between the screen display area and the patient for determining the visual field such that the screen display area is not directly visible to the patient.

6. The device as claimed in claim 1, further comprising a distance sensor for determining a relative distance between the eyes and the mirror and wherein the processing module is designed to establish the visual field of the patient depending on the relative distance of the eyes.

7. The device as claimed in claim 1, wherein the processing module is configured to display a sequence of test patterns on the screen, respectively determine the viewing direction of an eye of the patient when the test patterns are displayed and store said viewing direction assigned to the respective test pattern, and establish the visual field of the patient for one or both eyes on the basis of the viewing directions captured for the sequence of test patterns.

8. The device as claimed in claim 7, wherein the processing module is configured to dynamically adapt the sequence of test patterns depending on viewing directions captured for the patient.

9. The device as claimed in claim 1, wherein the processing module is configured to display one or more reference patterns on the screen, wherein the eye monitoring module is configured to capture reference patterns reflected from an eye of the patient and wherein the processing module is designed to determine the viewing direction of an eye of the patient, respectively, based on the reflected reference pattern.

10. The device as claimed in claim 1, wherein the processing module is configured to capture a reaction time of the patient, respectively depending on the eye movements, when the test patterns are displayed and to store spatially dependent reaction times in the visual field of the patient.

11. The device as claimed in claim 1, wherein the eye monitoring module is arranged on a side of the mirror facing away from the patient during the visual field test, and wherein the mirror has a point, placed in front of the eye monitoring module and permeable to light at at least specific wavelengths, for determining the eye movements.

12. The device as claimed in claim 1, wherein the eye monitoring module is arranged on a side of the mirror facing toward the patient during the visual field test and wherein the eye monitoring module is configured to determine the eye movements via the mirror.

13. The device as claimed in claim 1, wherein the eye monitoring module, is arranged with a direct line of sight to the eyes of the patient and outside of a mirroring surface of the mirror.

14. The device as claimed in claim 1, wherein the eye monitoring module comprises two image sensors and is configured to establish the eye movements of an eye in a stereoscopic fashion.

15. The device as claimed in claim 1, wherein the mirror is embodied with a non-planar mirror surface for increasing the field angle.

16. A method for determining a visual field of a patient, comprising the steps of:
- displaying test patterns on a screen,
- deflecting the test patterns from the screen to the eyes of the patient via a mirror aligned parallel to the bipupillary line of the patient for determining the visual field,
- capturing eye movements of the patient,
- determining viewing directions of the patient on the basis of the eye movements when the test patterns are displayed, and
- establishing the visual field of the patient on the basis of the viewing directions determined for the test patterns.

* * * * *